United States Patent [19]

Dietz et al.

[11] 4,419,190

[45] Dec. 6, 1983

[54] METHOD AND APPARATUS TO MEASURE THE OPERATING TEMPERATURE OF SOLID ELECTROLYTE-TYPE GAS SENSORS

[75] Inventors: Hermann Dietz, Gerlingen; Ferdinand Grob, Besigheim; Klaus Muller, Tamm; Lothar Raff, Remseck; Franz Rieger, Aalen; Hans-Martin Wiedenmann, Stuttgart, all of Fed. Rep. of Germany

[73] Assignee: Robert Bosch GmbH, Stuttgart, Fed. Rep. of Germany

[21] Appl. No.: 357,803

[22] Filed: Mar. 12, 1982

[30] Foreign Application Priority Data

May 6, 1981 [DE] Fed. Rep. of Germany ....... 3117790

[51] Int. Cl.³ .............................................. G01N 27/58
[52] U.S. Cl. .................................. 204/1 T; 204/408; 204/425
[58] Field of Search .................... 204/408, 1 S, 425

[56] References Cited

U.S. PATENT DOCUMENTS 4,356,065 10/1982 Dietz .................................... 204/1 T
4,376,026 3/1983 Hoffman et al. .................... 204/408

FOREIGN PATENT DOCUMENTS 2744844 2/1976 Fed. Rep. of Germany ...... 204/429
2711880 8/1978 Fed. Rep. of Germany ...... 204/429

Primary Examiner—G. L. Kaplan
Attorney, Agent, or Firm—Frishauf, Holtz, Goodman & Woodward

[57] ABSTRACT

To provide for temperature measurement of a solid electrolyte polarographic gas composition sensor, an ac signal is superimposed from an ac voltage source (2) on the applied voltage from a voltage source (1) if the sensor is a polarographic sensor, the ac signal being separated from the output by a filter combination (6, 7), the dc output being evaluated as usual, and the ac output being rectified in a rectifier (9) to obtain a measure of the temperature since the ac resistance ($R_{alt}$) is highly temperature dependent (see FIG. 3). The ac preferably is about 10% of the applied dc voltage, so that the voltage swing of the ac potential falls well within the linear range of output current with respect to voltage (see FIG. 2). The output from the ac channel (7, 9) to evaluate the temperature signal can be connected to a control loop circuit (10, 11), including a heater (11) to heat the sensor to maintain a uniform temperature thereof.

9 Claims, 3 Drawing Figures

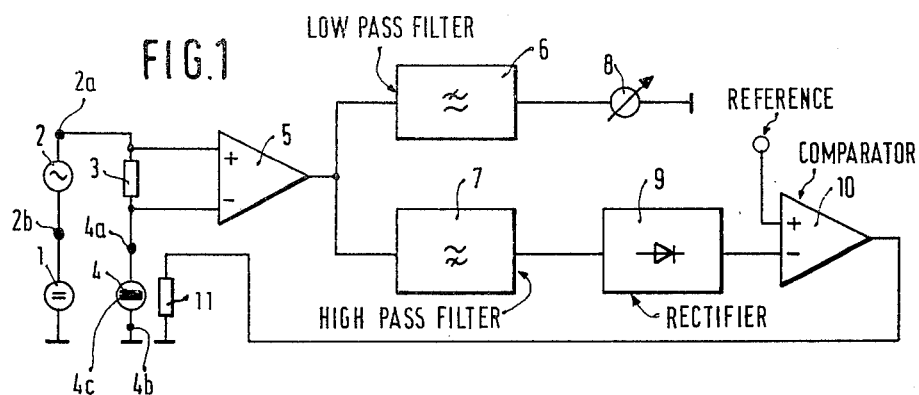
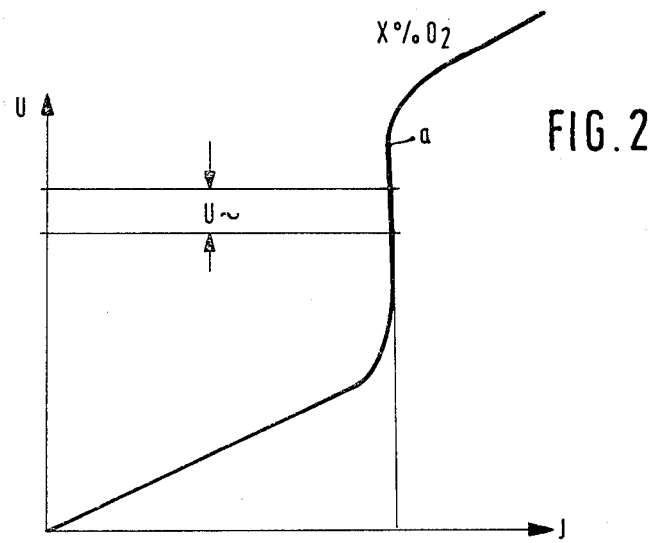
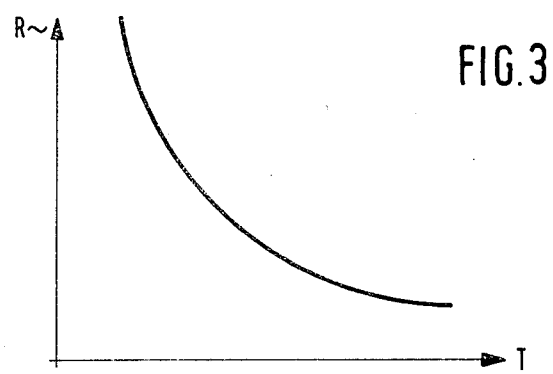

METHOD AND APPARATUS TO MEASURE THE OPERATING TEMPERATURE OF SOLID ELECTROLYTE-TYPE GAS SENSORS

Reference to related application, assigned to the asignee of the present invention: U.S. Ser. No. 213,049, filed Dec. 4, 1980, now U.S. Pat. No. 4,356,065; DIETZ. Reference to related literature: "Automotive Handbook" issued by Robert Bosch GmbH, First English Edition, Chapter on Exhaust Gas Sensors, pp. 275–277.

The present invention relates to sensors, and more particularly exhaust gas sensors of the solid electrolyte type, particularly adapted to determine the oxygen content in combustion exhaust gases and especially in the exhaust gases from automotive-type internal combustion engines.

Various types of sensors are utilized to determine the oxygen content of exhaust gases, and particularly for automotive use, the exhaust gases from internal combustion engines. There are two basic types. One type is the potentiometric sensor, also known as the lambda sensor, which is well known and the details of which are described, for example, in the referenced literature, "Automotive Handbook," issued by Robert Bosch GmbH, copyright 1976, chapter on exhaust gas sensors, pp. 275–277. Another type of sensor is the limit-current type sensor described, for example, in the referenced application, U.S. Ser. No. 213,049, filed Dec. 4, 1980, now U.S. Pat. No. 4,356,065; DIETZ.

It has previously been proposed to heat such sensors, and to control heating of the sensor so that it will be operating at a predetermined and essentially constant temperature. German Patent Disclosure Document DE-OS 27 44 844, Masaki, describes a current-limiting type sensor which can be connected to a current source and, after a predetermined temperature has been reached, a control system is connected which maintains the temperature of the sensor at an essentially constant level. The sensor includes a temperature sensor with which the temperature within the sensing range is measured. This arrangement requires a second sensing element within the sensing region of the sensor, to determine temperature, which is space consuming and additionally requires further electrical connections thereto. The space available for construction of the sensor is extremely limited. The number of connecting lines should be held to the minimum to prevent interference and to facilitate manufacture.

THE INVENTION

It is an object to provide a sensor system which is simple and reliable and which permits use of a current limiting-type sensor of the most simple construction to determine composition of a gas, and more particularly the oxygen content in exhaust gases from combustion processes especially from internal combustion engines.

Briefly, we have found that alternating current flow through the sensor is highly temperature dependent and that, consequently, applying ac in the order of about 1 kHz and up, for example 5 kHz can provide a temperature dependent signal. The sensor, which is a polarographic type is additionally connected to an electrical elevation circuit which evaluates an electrical characteristic thereof representative of combustion of the gas, as well known. These characteristics will vary with change of at least one component, for example oxygen, therein. The variation of the characteristic, for example output voltage of a potentiometric sensor or limit current flow in a limit-current type sensor will vary slowly, as the gas composition changes. In accordance with the present invention, the sensor electrodes have applied thereto an alternating current voltage of a frequency which is substantially in excess of the rate of variation of the electrical characteristics of the sensor, that is, of the output signal derived therefrom upon change in the gas composition. The magnitude of the alternating current flowing through the sensor is measured to obtain a measure of the temperature of the sensor. In accordance with a feature of the invention, a heating resistor is located close to the sensor, and the measured temperature signal is used to control heater current through the heater to maintain the sensor at a predetermined temperature.

The frequency of the alternating current, for example, can be in the order of at least 1 kHz. Preferably, the amplitude of the ac voltage applied to current-limiting sensors is less than the voltage across the sensor in the current-limiting range, for example about 10% of the applied dc voltage.

In accordance with a feature of the invention, the output signal representative of gas composition is separated from the ac component applied to the sensor by filters, that is, a low pass filter to provide a gas signal output and a high pass filter to derive the temperature signal which, after rectification, provides an analog dc signal output of sensor temperature, suitable for indication, or control purposes.

In potentiometric sensors, for example of a type described in the aforementioned literature reference, higher ac voltage may be used, provided the maximum current through the sensor is not exceeded.

The system has the advantage that the sensor itself forms the temperature measuring element and additional temperature measuring devices, such as thermocouples and the like, and their connections, are not needed. Further, the temperature is measured directly on the sensing element and is not falsified by additional components or structural elements associated with the sensor, for example, for its protection against contamination, hot exhaust gases, or the like.

The apparatus to measure the temperature of the sensor preferably utilizes a dc source as well as an ac source, the respective filters separating the dc and ac output signals from the sensor. This results in a simple supply and evaluation circuit using only well known and readily available commercial components. A current-measuring device, preferably, is a resistor connected in series with the voltage sources, across which a voltage drop can be obtained proportional to the current through the sensor. The thus obtained voltage drop is then separated into its low frequency or dc components and the much higher temperature sensing ac component by suitable low pass and high pass filters, the high pass filter then being connected to a rectifier. The output signal from the rectifier can be indicated on a measuring instrument or applied to a controller at the output of which a heater is connected to heat the sensor to a predetermined temperature level. The operating temperature of the sensor thus can be readily and simply maintained at an essentially constant level without additional sensing elements, such as thermocouples and the like, and their connecting lines.

DRAWINGS

FIG. 1 is a schematic circuit diagram of the system in accordance with the present invention;

FIG. 2 is a graph of current vs. voltage of a current-limiting type sensor for one predetermined oxygen level in a gas; and FIG. 3 is a graph of resistance to alternating current (ordinate) of a current-limiting type sensor with respect to temperature T.

The sensor itself is not described since it is known in the literature; see, for example, the above referenced application Ser. No. 213,049, now U.S. Pat. No. 4,356,065 to which published German Patent Disclosure Document DE-OS No. 27 11 880 corresponds. Such sensors, as only schematically shown in FIG. 1, have an ion conductive solid electrolyte body, for example, made of zirconium dioxide on which two electrodes, applied to different surface regions of the zirconium dioxide are applied. The electrodes are gas pervious, and have a measuring voltage applied thereto. Depending on the oxygen concentration in the gas to which the sensor is exposed, a higher, or lower diffusion limiting current will establish itself which, as well known, is limited by the diffusion rate of the oxygen molecules which reach the electrodes. Sensors of this type, when exposed to the exhaust gas from a combustion process, for example, when positioned in the exhaust manifold or exhaust gas system of an internal combustion engine, have an operating characteristic as shown in FIG. 2. The current measured through the sensor is shown with respect to voltage (ordinate). For any given oxygen level, the current is steady or constant over a certain measuring voltage region applied to the electrodes. For a detailed discussion, the aforementioned Dietz application and patent are referred to. For optimum operation, current emitting-type sensors should operate at between 500° C. and 700° C., and should be heated to that temperature range, in order to hold the exchange current at a higher level than the limiting current determined only by the diffusion.

The current-limiting sensor provides output values which are essentially independent of temperature within a range of about 100° C. Temperature and speed of application, or rate of application of the measured gas to the sensor are, however, subject to wide variations. It is, therefore, desirable to maintain the sensor at a temperature independent of that of the gas to be sensed, and to provide for independent temperature control thereof.

The current limiting-type sensor is an element which responds not only to changes in oxygen level but also to changes in voltage. Thus it responds to two different parameters. The dynamic behavior of current-limiting sensors with respect to voltage changes is highly dependent on frequency, that is, the frequency of the voltage applied to the sensor. At low frequencies, the sensor current within the region a of FIG. 2 is essentially independent of changes in frequency. As the frequency increases, however, current changes will result which, at frequencies of about 1 kHz, or more, will become proportional to the changes in applied voltage.

It is thus possible to form a relationship of the resistance of the element with respect to frequency of applied voltage. The resistance to alternating current has been found to be less than the dc resistance of the electrode system. The resistance to alternating current, $R_{alt}$, is highly temperature dependent and, upon increasing temperature, is similar to a decreasing e function, as illustrated in FIG. 3.

Other types of oxygen sensors which use a solid electrolyte, such as the lambda sensors described in the aforementioned literature reference, exhibit a similar effect.

The different behavior of resistance of the solid electrolyte body with respect to applied voltage when the voltage is either steady, or varies at a rate of about 1 kHz or more can be used to determine the temperature of the sensor and to derive an output signal which, in turn, can be indicated or applied to control heating of the sensor such that a predetermined command or desire temperature is being maintained.

In accordance with the present invention, an ac voltage source is applied to the sensor, which is a current-limiting sensor. In a current-limiting sensor, the a-c voltage is additionally or serially connected to the d-c voltage supply (see FIG. 1). The a-c voltage proportion of the applied voltage is essentially independent on oxygen concentration. In a current-limiting sensor, the limit current is independent of voltage within the range a, as seen in FIG. 2. (In a potentiometric sensor, the output voltage is essentially unaffected by the superposed ac.) The dc component thus is not changed by addition of an ac voltage source, so that the output signal representative of oxygen concentration can be used, as well known and as customary to determine the oxygen concentration of the gas to which the sensor is exposed. The alternating current, however, the magnitude of which is determined only by the alternating current resistance, $R_{alt}$, of the sensor can be filtered out and separated from the dc component, or the slowly varying dc component so that the ac flowing can be utilized as a parameter or value representative of temperature and thus employed for indication or control purposes.

The amplitude of the alternating voltage, in current-limiting sensors, is limited only by the magnitude of the current-limiting range a of FIG. 2. Amplitude values of alternating voltages in the order of about 10% of dc voltage have been found suitable, see FIG. 2, $U\sim$, which shows the superposition or modulating range of the a-c voltage on the applied d-c voltage required for limit current operation of the sensor.

The alternating current for the polarographic or current-limiting sensor is above 1000 Hz; frequencies in the order of about 5 kHz have been found eminently suitable. FIG. 1 illustrates a temperature control system. A dc source 1 and ac source 2 having terminals 2a, 2b are serially connected. The series connection of the dc source and the ac source is connected to a resistor 3 which, in turn, is serially connected with a polarographic sensor 4, for example, of the type of the above referenced Dietz patent. The sensor 4 has a solid electrolyte body 4c and two electrodes 4a, 4b applied thereto. As can be seen, dc source 1, ac source 2, resistor 3 and sensor 4 form a closed current loop network. A comparator, or differential amplifier 5 is connected across the resistor 3. The differential amplifier 5 has its output connected to two channels. One channel has a loss pass filter 6 therein, which is connected to a measuring element 8; rather than using a measuring element, other control systems, or other utilization apparatus can be connected thereto, for example, to control the air/fuel ratio of an internal combustion engine, the exhaust gases of which are to be measured by the sensor 4; or to control the air/fuel supply of a burner or furnace system. The second channel connected to the output of the differential amplifier 5 is formed by a high pass filter 7, connected to a rectifier 9. The output of the rectifier 9 is connected to the inverting input of a comparator, which, for example, may be formed by an operational amplifier, a differential amplifier or the like. The direct input receives a reference value, for example derived from a potentiometer connected to a regulated source of voltage supply and applying a voltage to the comparator 10 representative of a predetermined temperature value of the sensor. The comparator 10 then controls the heating resistor 11, located adjacent the sensor or forming part of an assembly thereof in accordance with any known and suitable structure, to heat the sensor, or sensing region of the sensor 4. Suitable amplification apparatus between the comparator 10 and the heater 11, and connecting and buffer amplifiers have been omitted for clarity and can be used in accordance with well known circuit design.

OPERATION

A voltage will be dropped across the resistor 3 which has a dc component and ac component superimposed thereon. The dc component is representative of the oxygen concentration of the sensor 4. The ac component will be determined by the ac resistance $R_{alt}$ of the sensor 4, and is temperature dependent. This voltage is sensed by the differential amplifier 5 and amplified. Low pass filter 6 suppresses the ac components of the voltage at resistor 3. The low pass filter 6 is so designed that the frequency of ac voltage 2 cannot pass through the low pass filter 6. The instrument 8, thus, will have applied thereto a voltage which is representative of oxygen concentration of the sensor 4, for indication or for application for further control functions.

The high pass filter 7 is so designed that it rejects dc components. Only ac voltage components are passed thereby. To provide for improved signal-to-noise rejection, it is also possible to utilize a band pass filter rather than a high pass filter, and designed to pass the frequency of the high frequency source 2, but to suppress all others.

The pure ac signal component is rectified by rectifier 9 which, preferably, is a peak value rectifier. The output signal derived from rectifier 9, then, will be temperature dependent. This signal is suitable for temperature indication, or for further control functions. As shown, the comparator 10 receives the output signal from the peak rectifier 9, and compares this output signal with a reference to so control the heating resistor 11 that the temperature of the sensor 4 remains at a constant, and command value. Variations in temperature and rate of application of the sensing gas, which also affect temperature therefore can be compensated, so that the temperature of the sensor will not leave a predetermined operating range. An analog output can be obtained, as explained in the referenced Dietz patent.

Various changes and modifications can be made within the scope of the inventive concept.

We claim:

1. Method of measuring the operating temperature of a limit current-type solid electrolyte gas composition sensor (4) having two electrodes (4a, 4b), wherein the electrical characteristic of the sensor, representative of combustion of the gas, varies with change of at least a component thereof, and said change is evaluated; comprising, in accordance with the invention, the steps of applying to the electrodes of the sensor (4) a direct voltage and, serially therewith, an alternating voltage of a frequency substantially in excess of the rate of variation of said electrical characteristic and of an amplitude which is substantially less than the range of direct voltage within which the current through the sensor is essentially independent of applied direct voltage and depends only on concentration of said gas;

and measuring the magnitude of alternating current flowing through the sensor to obtain a measure of the temperature thereof.

2. Method according to claim 1, wherein the amplitude of the alternating current voltage is in the order of about 10% of direct current voltage applied to the sensor.

3. Method according to claim 1, wherein the frequency of the alternating current voltage is in the order of approximately 5000 Hz.

4. Method according to claim 1, further including the step of providing a heater element (11) located adjacent the sensor (4);

and controlling the heat output of said heater element as a function of the measured alternating current flowing through the sensor with respect to a reference to maintain the temperature of the sensor at an essentially uniform level.

5. Apparatus to determine the operating temperature of a solid electrolyte limit current-type or polarographic-type gas composition sensor (4) having two electrodes (4a, 4b);

said apparatus including a d-c current source (1) connected to the electrodes;

means (6, 7) for evaluating an electrical characteristic of the sensor representative of the composition of the gas and varying with change of at least one component thereof, and comprising an alternating current voltage source (2) serially connected with the d-c current source and the electrodes of the sensor (4a, 4b);

current measuring means (3, 5) connected to the sensor and measuring current flow therethrough, the d-c current source (1), the a-c voltage source (2), the current measuring means (3) and the sensor (4) being connected in a closed series circuit, and the a-c voltage from said a-c source (2) being superimposed on, or modulating the d-c voltage; and frequency separating means (6, 7) connected to the output of said current flow measuring means and separating alternating current components and essentially direct current or slowly varying current components, and deriving, respectively, direct output signals representative of the at least one component in the composition of the gas, and alternating current components representative of temperature of the gas, the level of a-c voltage applied from the a-c source being of an amplitude which is substantially less than the range of direct voltage within which the current through the sensor is essentially independent of applied direct voltage.

6. Apparatus according to claim 5, wherein said frequency separating means (6, 7) comprises a low pass filter (6) to separate direct current or slowly varying dc components; and a high pass filter (7) to separate alternating current components from the output of the current flow measuring means.

7. Apparatus according to claim 5, wherein the a-c voltage source has a frequency output of about at least 1000 Hz;
and the frequency separation means includes a high pass filter passing frequencies matched to the output of said a-c voltage source.

8. Apparatus according to claim 7, wherein the frequency of said voltage source (2) is in the order of about 5 kHz.

9. Apparatus according to claim 5, wherein the amplitude of the voltage output from the a-c voltage source is in the order of about 10% of the voltage applied by the d-c voltage source.

* * * * *